(12) United States Patent
Riera Giner et al.

(10) Patent No.: US 11,071,802 B2
(45) Date of Patent: Jul. 27, 2021

(54) DEVICE FOR DIFFUSING VOLATILE SUBSTANCES

(71) Applicant: Zobele Espana, S.A., Barcelona (ES)

(72) Inventors: Montserrat Riera Giner, Barcelona (ES); Ruben Garcia Fabregas, Barcelona (ES); Elisabeth Martinez de Morentin Pujabet, Barcelona (ES); Cedric Gobber, Barcelona (ES)

(73) Assignee: ZOBELE ESPANA, S.A., Barcelona (ES)

( * ) Notice: Subject to any disclaimer, the term of this patent is extended or adjusted under 35 U.S.C. 154(b) by 0 days.

(21) Appl. No.: 14/901,609

(22) PCT Filed: Mar. 31, 2014

(86) PCT No.: PCT/ES2014/070243
§ 371 (c)(1),
(2) Date: Dec. 28, 2015

(87) PCT Pub. No.: WO2014/207273
PCT Pub. Date: Dec. 31, 2014

(65) Prior Publication Data
US 2016/0129146 A1 May 12, 2016

(30) Foreign Application Priority Data
Jun. 26, 2013 (EP) ..................................... 13382245

(51) Int. Cl.
*A61L 9/12* (2006.01)

(52) U.S. Cl.
CPC ......... *A61L 9/125* (2013.01); *A61L 2209/134* (2013.01); *A61L 2209/15* (2013.01)

(58) Field of Classification Search
CPC .............. A61L 9/125; A61L 2209/134; A61L 2209/15; A61L 2209/133; A61L 2209/10;
(Continued)

(56) References Cited

U.S. PATENT DOCUMENTS 4,157,787 A 6/1979 Schwartz
4,849,606 A 7/1989 Martens, III et al.
(Continued)

FOREIGN PATENT DOCUMENTS

EP 0722742 A2 7/1996
EP 0722743 A2 7/1996
(Continued)

*Primary Examiner* — Joseph A Greenlund
*Assistant Examiner* — Juan C Barrera
(74) *Attorney, Agent, or Firm* — Hayes Soloway PC

(57) ABSTRACT

The device for diffusing volatile substances, comprising a casing (1) wherein at least two respective volatile substance containers (2) are housed, said containers (2) being moveable relative to said casing (1) between at least one first position, where one of the containers (2) is exposed to the environment for diffusing its volatile substances, and a second position, where another container (2) is exposed to the environment, and characterised in that between said casing (1) and the container or containers (2) unexposed to the environment a space (3) is defined, which allows the diffusion of volatile substances from the unexposed container or containers (2) to a lesser extent than the container (2) exposed to the environment.
It enables performance to be improved due to the fact that two or more fragrances in two or more containers contribute to the final performance and intensity.

11 Claims, 4 Drawing Sheets

(58) Field of Classification Search
CPC ...... A61L 9/035; A61L 9/04; A61L 2209/111; A61L 9/12; A61L 9/048; B60H 2003/0064; B60H 3/0007; Y10S 261/88; A01M 1/2055; A01M 1/2044; A01M 29/12
USPC ...................................................... 239/34–60
See application file for complete search history.

(56) References Cited

U.S. PATENT DOCUMENTS

| | | | |
|---|---|---|---|
| 5,050,798 A | 9/1991 | Sullivan | |
| 5,178,327 A | 1/1993 | Palamand | |
| 5,518,790 A | 5/1996 | Huber et al. | |
| 5,695,692 A * | 12/1997 | Kennedy | A61L 9/122 239/60 |
| 5,805,768 A * | 9/1998 | Schwartz | A61M 15/0045 261/DIG. 65 |
| 6,581,915 B2 * | 6/2003 | Bartsch | A01M 1/2033 261/104 |
| 6,790,408 B2 | 9/2004 | Whitby et al. | |
| 7,011,795 B2 * | 3/2006 | Thompson | A61L 9/035 222/167 |
| 2002/0068010 A1 * | 6/2002 | Laudamiel-Pellet | A01M 1/2033 422/5 |
| 2003/0164557 A1 * | 9/2003 | Chung | A61L 9/035 261/26 |
| 2004/0180070 A1 | 9/2004 | Inoue | |
| 2005/0285538 A1 | 12/2005 | Jaworski et al. | |
| 2006/0153744 A1 | 7/2006 | Thompson et al. | |
| 2008/0093474 A1 * | 4/2008 | Suissa | A61L 9/122 239/34 |
| 2009/0212124 A1 * | 8/2009 | Kenny | A01M 1/2044 239/58 |

FOREIGN PATENT DOCUMENTS

| | | |
|---|---|---|
| EP | 1854647 A1 | 11/2007 |
| EP | 2347922 A1 | 7/2011 |
| ES | 22759601 T3 | 6/2007 |
| WO | 2004105878 A1 | 12/2004 |
| WO | 2007110086 A1 | 10/2007 |

* cited by examiner

DEVICE FOR DIFFUSING VOLATILE SUBSTANCES

The present invention relates to a device for diffusing volatile substances, particularly to a device wherein two or more volatile substances are diffused by a passive diffusion system.

BACKGROUND OF THE INVENTION

Passive systems for diffusing volatile substances are known. Passive diffusers are devices for evaporating volatile substances in a closed environment, without using electric power, heating elements, or absorption wicks, for the purpose of simplifying and minimising the cost of the device, but maintaining at the same time its effectiveness, and allowing the user to adjust the evaporation rate of said product.

Such devices are especially designed to be used in cooperation with an air stream at a suitable temperature, improving the evaporation and diffusion of the volatile substances.

Some of these devices include semi-permeable membranes which allow the outlet of vapours but prevent the escape of liquid. These devices consist of a container comprising a formed portion and a membrane. When the membrane is flat, the formed portion is designed so that it includes a flat circumferential lip, wherein the formed portion and the membrane are welded together. The formed portion is designed so that it can contain a sufficient amount of liquid, gel or solid substance.

These devices are inexpensive and clean, since they prevent the substance from spilling in the event of unsuitable handling, and in their simplest applications they do not include any extra housing, such as, for instance, in U.S. Pat. Nos. 4,157,787 and 5,518,790.

In other cases, this container is usually inside a plastic housing, which acts as protection and support. The housing also contributes to a better presentation of the product. An example of these housing devices is described in U.S. Pat. No. 4,849,606.

Patent application US-2006153744 describes a device having a multiple fragrance solution, which comprises a cartridge for dispensing aromas in a room. The cartridge has a plurality of aromatic elements supported on a rotating disk, said disk being housed in a cavity of a housing, which forms an air inlet and an outlet port.

U.S. Pat. No. 6,790,408 B2 describes a method and a device for preventing the habituation of a fragrance. The method and the device are adapted in order to provide a space with a continuous diffusion of a first fragrance and a periodic diffusion of a second fragrance. These fragrances can be vaporised by heating.

U.S. Pat. No. 7,011,795 B2 describes a device for diffusing aromas in a room. The device comprises a cartridge having a plurality of aromatic elements mounted on a rotating disk, a motor, a blower and some sensors, the blower generating an air flow in order to spread the fragrance.

These devices, however, have a series of drawbacks, which are listed below.

On the one hand, most of these are devices which need to be connected to the grid, with the disadvantage of very poor portability and a high cost. On the other hand, the performance of the prior solutions is limited due to the total surface of the chemical compounds exposed to the air, and considering passive diffusion systems, they do not have any noticeable effect for the users or any enhancing effect.

Therefore, the present invention aims to solve the problems of the prior devices by providing a device which improves performance, allows an enhancing effect and creates a noticeable effect among users working with a passive diffusion system for evaporating volatile substances.

DESCRIPTION OF THE INVENTION

The solution of the aforesaid disadvantages is achieved with the device of the invention, presenting other advantages described below.

The device for diffusing volatile substances, comprising a casing where at least two containers of respective volatile substances are housed, said containers being movable relative to said casing between at least one first position, where one of the containers remains exposed to the environment for diffusing its volatile substances, and a second position, where another container is exposed to the environment, and is characterised in that between said housing and the container or containers exposed to the environment a space is defined, which allows the diffusion of volatile substances from the unexposed container or containers, to a lesser degree than from the container exposed to the environment.

Advantageously, the device for diffusing volatile substances according to the present invention also comprises a motor which drives the movement of said containers, said motor being drivable preferably by batteries.

If desired, the device for diffusing volatile substances according to the present invention may comprise a position detector for detecting the position of said containers relative to the casing and/or a presence detector for detecting the presence of said containers inside the casing.

According to a first embodiment, said containers are arranged on a rotating disk, and advantageously the thickness of said rotating disk is lesser than the width of said space.

Furthermore, said presence detector is preferably attached to a central projection of said rotating disk.

According to a second embodiment, said containers are arranged on a rotating support provided with a plurality of holes, and said rotating support comprises at least two vertical housings separated by a wall, one housing for every container, said wall having a lesser height than the height of said containers.

The ratio between the surface defined by said space and the surface of the exposed container or containers, whereby the volatile substances evaporate, is preferably comprised between 1% and 50%, particularly between 10% and 20%.

That is, this ratio is between the evaporation surface of volatile substances in the exposed container or containers and the evaporation surface of volatile substances in the unexposed container or containers. In the case of the unexposed container or containers, volatile substances evaporate through the surface defined by said space.

In the present invention, performance is improved due to the fact that two or more fragrances in two or more containers contribute to the final performance and intensity. Hidden fragrances contribute to the final performance, remarkably reducing the overall size of the device.

With the device of the present invention an enhancing effect can be generated due to the fact that, in addition to diffusing volatile substances from the exposed container, volatile substances from the rest of containers, which are unexposed to the environment, are also diffused, to a lesser extent.

Moreover, a noticeable effect for the user can be generated with the device of the present invention due to the change of fragrance, thus preventing the habituation of a fragrance, and with a passive diffusion system.

BRIEF DESCRIPTION OF THE DRAWINGS

For a better understanding of what has been disclosed, some drawings in which a practical case of embodiment is shown, schematically and solely by way of non-limiting example, are attached.

DESCRIPTION OF A PREFERRED EMBODIMENT

Figure 1:
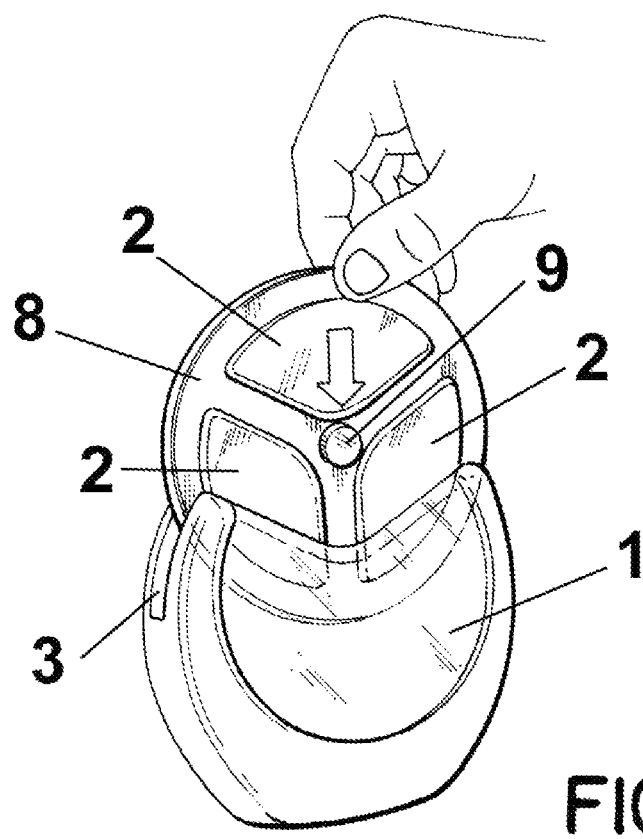
FIG. 1 is a perspective view of the device for diffusing volatile substances according to a first embodiment.

FIGS. 1 to 5 show a first embodiment of the device for diffusing volatile substances, comprising a casing 1 wherein a disk 8 provided with a plurality of volatile substance containers 2 is inserted.

Said disk 8 may include two or more containers 2, for example, three, as in the embodiment shown in the drawings. Each container 2 contains a different volatile substance, for example, an air freshener or insecticide substance with different aromas or attributes.

Containers 2 have features that allow the diffusion of the volatile substances, the former being formed, for example, by membranes or a similar material.

As can be seen particularly in FIG. 1, said disk 8 is manually housed inside a space 3, so that typically one of said containers 2 remains completely exposed to the environment. However, the other unexposed containers 2 do not remain hermetically sealed, but only partially enclosed by the casing wall 1 to reduce evaporation and diffusion of the volatile substances, since the thickness of said disk 8 is lesser than the width of said space 3, thus creating a space, as better seen in FIG. 5.

This space 3 allows volatile substances from the unexposed containers 2 to also diffuse to the environment, although to a lesser extent than the volatile substances from the exposed container 2.

Moreover, volatile substances from said containers 2 can be accumulated and mixed in this space 3, as explained hereinafter.

The ratio between the surface defined by said space 3 and the surface of the exposed container or containers, whereby the volatile substances evaporate, is comprised between 1% and 50%, particularly between 10% and 20%.

That is, the volume remaining in front of the evaporation surface of the unexposed container or containers 2 defines the space 3 wherein the vapours of the volatile substances are accumulated, and the surface defined by said space 3 corresponds to the exchange surface between the volume of this space 3 and the environment.

Said disk 8 rotates relative to the casing 1, either manually or automatically, so that it is possible to vary the container 2 exposed to the outside of the casing 1.

Said rotational movement of the rotating disk 8 is preferably automatically performed, and the device of the present invention comprises thereto a motor 4 powered by batteries 5 and a reduction gear system 14, 15 to reduce the motor speed 4 and increase the torque.

In order to know at all times the relative position of the rotating disk 8 relative to the casing 1, the disk 8 comprises a position detector 6 in contact with a central projection 9 of the disk 8.

Said position detector 6 is formed by a lever which can be placed in at least two positions.

Figure 2:
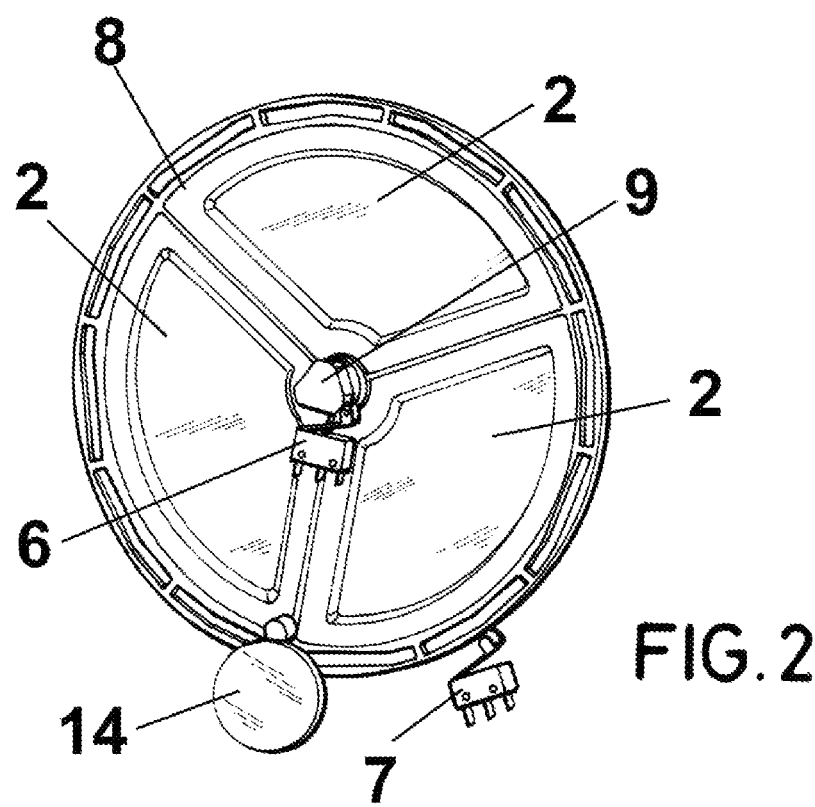
FIG. 2 is a perspective view of the rotating disk from the device for diffusing volatile substances of the first embodiment, including the position and presence sensors and the gear which rotates said disk.

As can be better seen in FIG. 2, said central projection 9 is substantially triangular, with rounded vertices, so that the position detector 6 detects whether the lever is in a first position (corresponding to one of the vertices of said central projection 9) or in a second position (corresponding to the sides defined by the central triangular projection 9).

Furthermore, the device of the present invention comprises a presence detector 7 which detects the presence of the rotating disk 8 inside said space 3.

Figure 3:
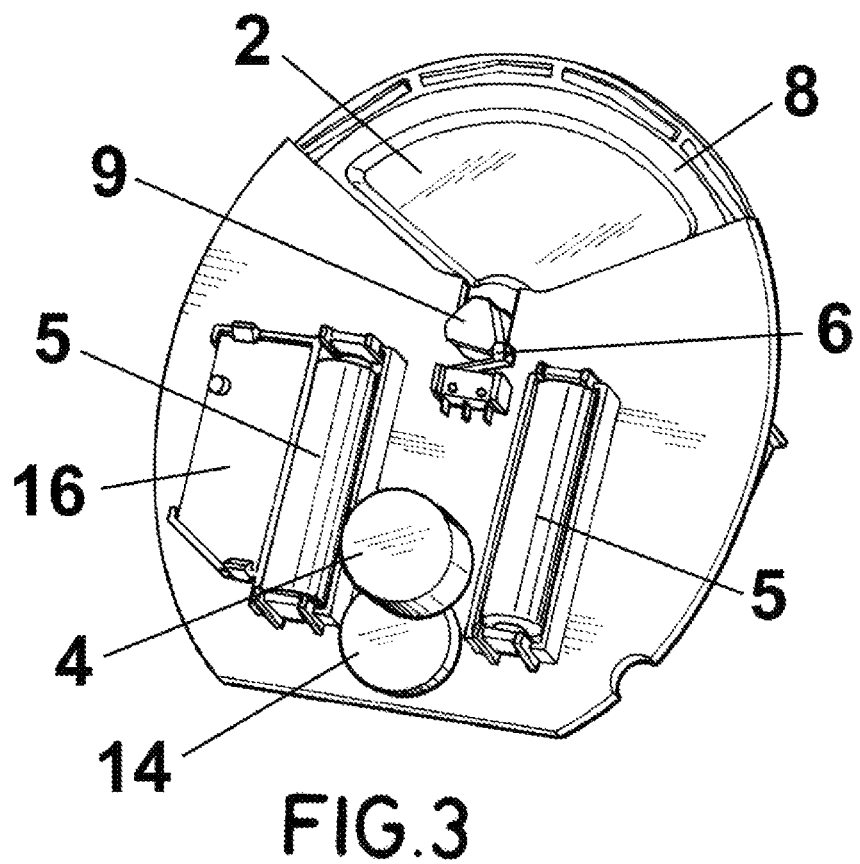
FIG. 3 is a perspective view of the rotating disk of the device for diffusing volatile substances of the first embodiment, including the motor, batteries and the printed circuit board.
Figure 4:
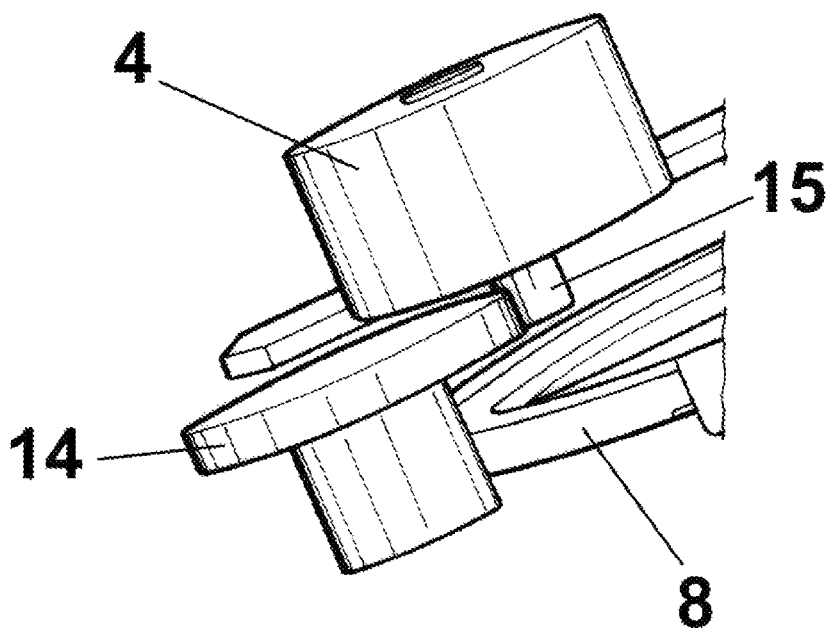
FIG. 4 is a perspective view of the system which transmits the rotational movement to the disk.
Figure 5:
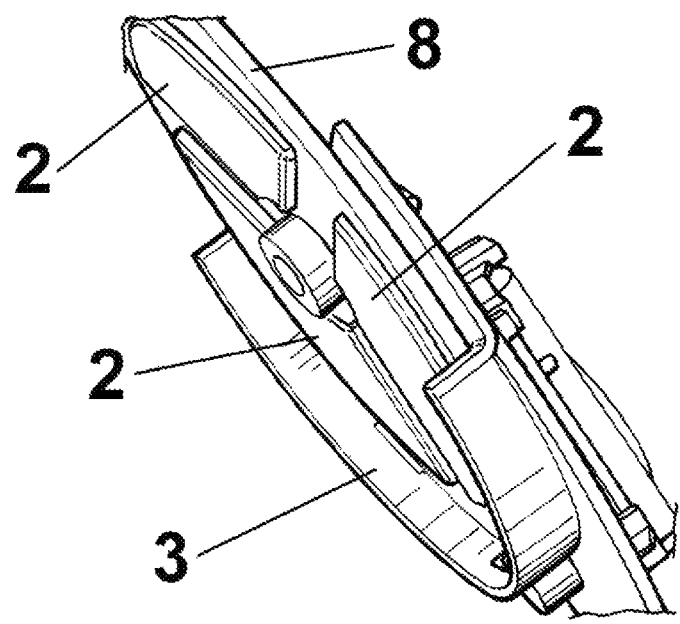
FIG. 5 is a perspective view of the rotating disk inserted in the slot of the device of the present invention.

In order to control the automatic movement of the rotating disk 8, the device of the present invention comprises electronic control means, represented in FIG. 3, via a printed circuit board 16.

The device works as follows: First, a user introduces the rotating disk 8 in the space 3 of the casing 1 and the presence detector 7 detects the presence of said rotating disk 8. Then, the electronic control means send drive signals to the motor for driving the rotation of the disk 8 at predetermined intervals. For example, the number of movements per day could be between 480 and 1.

When the disk 8 rotates, the accumulation of said volatile substances from the container 2 is diffused to the outside, generating an enhancing effect.

Furthermore, when the disk 8 is stopped, not only volatile substances from the container 2 exposed to the environment will be diffused to the outside, but also volatile substances from other containers 2 unexposed to the environment.

It should be noted that, although not shown in the drawings, the evaporation of volatile substances can be accelerated by using heating elements.

Figure 6:
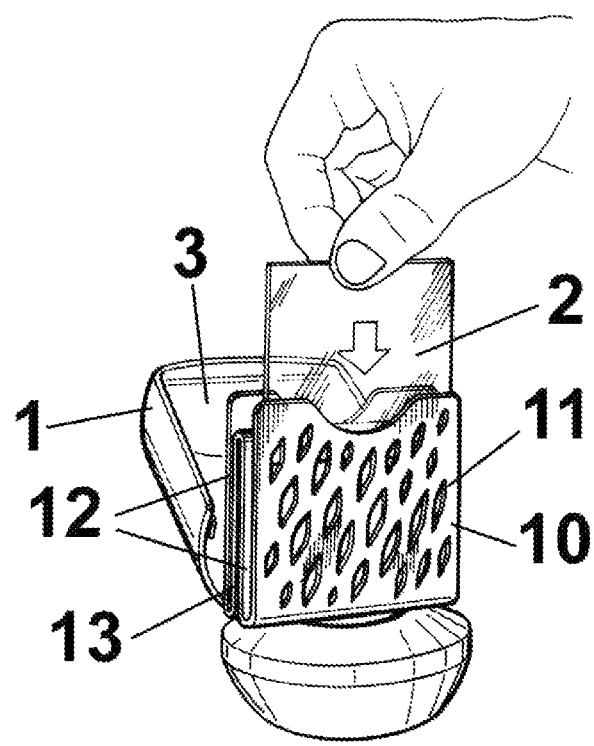
FIG. 6 is a perspective view of the device for diffusing volatile substances according to a second embodiment during the insertion of one of the volatile substance containers.
Figure 7:
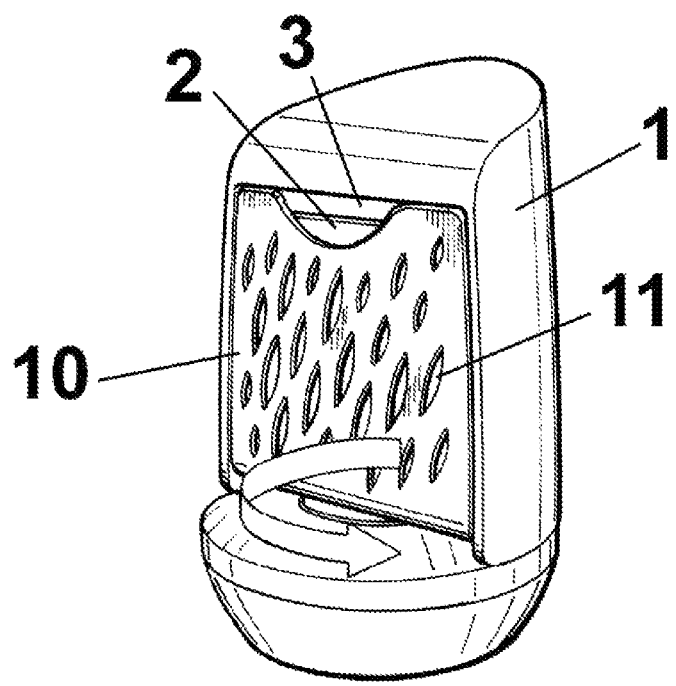
FIG. 7 is a perspective view of the device of the present invention according to said second embodiment with the rotating support in a first position.
Figure 8:
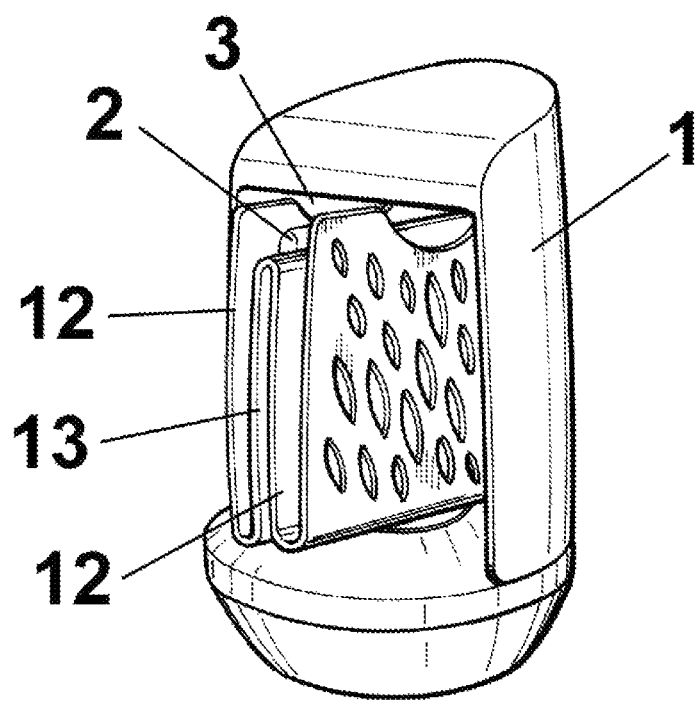
FIG. 8 is a perspective view of the device of the present invention according to said second embodiment with the rotating support in a second position, turned 90° from the one shown in FIG. 7.

FIGS. 6 to 8 show a second embodiment of the device according to the present invention. For the sake of simplicity, in this second embodiment the same numerical references as in the first embodiment are used to indicate equivalent elements.

In this second embodiment, the device also comprises a casing 1 wherein several containers 2 are inserted, two in case of the represented embodiment. These containers 2 are housed in vertical housings 12 of a rotating support 10 said rotating support 10 comprising holes 11 for diffusing volatile substances.

In this embodiment, the housing 1 defines in its interior a space 3 delimited by said rotating support 10, as shown, particularly, in FIG. 6.

Said vertical housings 12 are separated by a vertical wall 13, the height of said vertical wall 13 being less than the height of said containers 2, so that there is a mixture of the volatile substances from both containers 2. That is, the volatile substances from the container 2 placed adjacent to said holes 11 will diffuse more than the volatile substances from the other container 2, which will accumulate in said space 3, in the rotating support 10 position represented in FIG. 7.

As in the previous embodiment, when the rotation of said rotating support 10 (FIG. 8) occurs, the mixture of the volatile substances accumulated in the space 3 will diffuse to the outside, generating an enhancing effect.

Although not shown in the drawings for the sake of simplicity, it must be noted that the rotation of said support 10 can be performed automatically by a motor, a reduction gear system and control means similar to those described regarding the first embodiment.

Furthermore, the evaporation of volatile substances could also in this case be increased by the placement of a heating element.

Although reference has been made to a specific embodiment of the invention, it is apparent to a person skilled in the art that the device described is susceptible to numerous variations and modifications, and that all the details mentioned can be replaced by others that are technically equivalent, without departing from the scope of protection defined by the appended claims.

The invention claimed is:

1. A device for diffusing volatile substances, comprising a static casing that contains a first volatile substance container containing a first volatile substance and a second volatile substance container containing a second volatile substance and an outlet in an upper portion of the static casing, wherein the first volatile substance container and the second volatile substance container are moveable relative to said static casing between at least one first position, wherein the first volatile substance container is at least partially positioned beyond the outlet and outside the static casing and is exposed to an environment for diffusing the first volatile substance and the second volatile substance container is unexposed for diffusing the second volatile substance to a lesser extent, and a second position, wherein the second volatile substance container is at least partially positioned beyond the outlet and outside the static casing and is exposed to the environment and the first volatile substance container is unexposed, characterised in that between said static casing and the container or containers unexposed to the environment a space is defined for the volatile substances from the exposed container and the unexposed container to diffuse directly through the outlet and exit the device into an external environment.

2. The device for diffusing volatile substances according to claim 1, further comprising a motor which drives the movement of said containers.

3. The device for diffusing volatile substances according to claim 2, wherein said motor is drivable by batteries.

4. The device for diffusing volatile substances according to claim 1, comprising a position detector which detects the position of said containers relative to the casing.

5. The device for diffusing volatile substances according to claim 4, wherein said position detector is attached to a central projection of a rotating disk.

6. The device for diffusing volatile substances according to claim 1, comprising a presence detector which detects the presence of said containers inside the casing.

7. The device for diffusing volatile substances according to claim 1, wherein said containers are arranged on a rotating disk and the rotating disk is partially contained within the static casing.

8. The device for diffusing volatile substances according to claim 7, wherein the thickness of said rotating disc is less than the width of said space defined in said casing.

9. The device for diffusing volatile substances of claim 7, wherein said static casing and said rotating disk are oriented vertically and said rotating disk is rotatable on a horizontal axis.

10. The device for diffusing volatile substances according to claim 1, wherein a ratio between the surface defined by said space and a surface of the exposed container or containers whereby the volatile substances evaporate is comprised between 1% and 50%.

11. The device for diffusing volatile substances according to claim 10, wherein the ratio between the surface defined by said space and the surface of the exposed container or containers whereby the volatile substances evaporate is comprised between 10% and 20%.

* * * * *